United States Patent [19]

Hayashi et al.

[11] Patent Number: 4,721,713

[45] Date of Patent: Jan. 26, 1988

[54] PROCESS FOR INHIBITING BLOOD PLATELET AGGREGATION AND PROMOTING VASODILATION

[75] Inventors: Eiichi Hayashi; Noriyasu Takayanagi; Katsumi Nishimura; Masao Yaso; Yukio Suzuki, all of Shizuoka, Japan

[73] Assignee: Toyo Jozo Kabushiki Kaisha, Shizuoka, Japan

[21] Appl. No.: 58,890

[22] Filed: Jun. 5, 1987

[30] Foreign Application Priority Data

Feb. 20, 1986 [JP] Japan ................................ 61-36197

[51] Int. Cl.$^4$ ........................................... A61K 31/495
[52] U.S. Cl. ..................................... 514/255; 514/822; 514/929
[58] Field of Search .................... 514/255, 822, 929

[56] References Cited

U.S. PATENT DOCUMENTS 3,720,768  3/1973  Jones et al. .................... 514/255
4,599,413  7/1986  Kikumoto et al. .............. 514/255

OTHER PUBLICATIONS

Jones; J. Am. Chem. Soc. 71: pp. 78–81 (1949).

*Primary Examiner*—Allen J. Robinson
*Attorney, Agent, or Firm*—Young & Thompson

[57] ABSTRACT

A method for inhibiting blood platelet aggregation in humans, and promoting vasodilation in humans, by administering to a human in need of the same an effective amount of 2-hydroxy-3-isopropyl-5,6-dimethylpyrazine or a hydrate or a pharmaceutically acceptable non-toxic salt thereof. Administration can be orally in an amount of about 0.02–12 mg/kg body weight per day, or parenterally in an amount of about 0.01–6 mg/kg of body weight per day.

6 Claims, 1 Drawing Figure

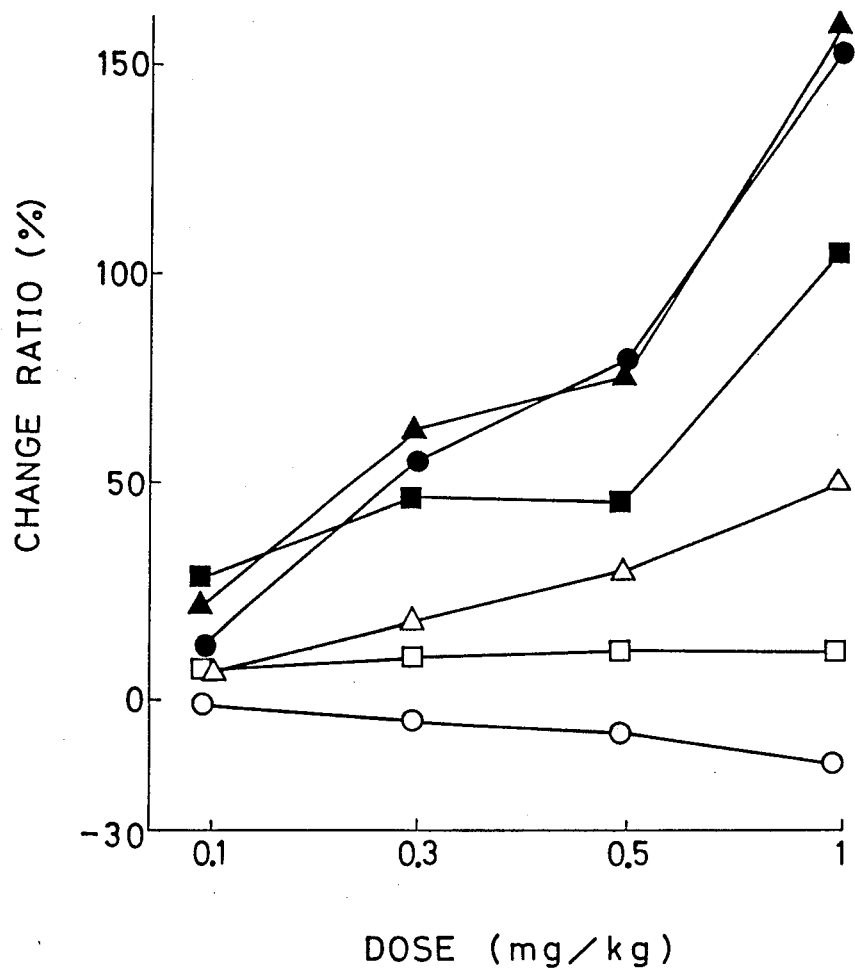

PROCESS FOR INHIBITING BLOOD PLATELET AGGREGATION AND PROMOTING VASODILATION

FIELD OF THE INVENTION

The present invention relates to a pharmacological process for inhibiting blood platelet aggregation and promoting vasodilation.

BACKGROUND OF THE INVENTION

It is known to inhibit blood platelet aggregation by administering compounds having a pyrazine ring as a main nucleus. Thus, tetramethyl pyrazine has been proposed for this purpose [Abstract of the 16th Congress of Heterocyclic Chemistry (Osaka), pp. 65–68 (1984)], as have also 2-higher fatty acyloxymethyl pyrazines (Japanese Unexam. Publ. KOKAI No. 59-219269).

On the other hand, 2-hydroxy-3-isopropyl-5,6-dimethylpyrazine is a known compound which has been synthesized by Reuben G. Jones [J. Am. Chem. Soc., 71: 78–81 (1949)]. However, the pharmacological activity thereof was unknown.

OBJECTS OF THE INVENTION

It is an object of the present invention to provide a method for inhibiting blood platelet aggregation by administration of a compound having low toxicity.

Another object of the present invention is the provision of a method for promoting vasodilation by the administration of a compound having low toxicity.

SUMMARY OF THE INVENTION

It has now been found that 2-hydroxy-3-isopropyl-5,6-dimethylpyrazine or a hydrate or a pharmaceutically acceptable non-toxic salt thereof has an inhibitory effect on blood platelet aggregation and promotes the blood flow in organs and tissues, as well as having a protective effect against anoxia.

Examples of pharmaceutically acceptable non-toxic salts are inorganic or organic salts such as the hydrochloride, sulfate, carbonate, nitrate, hydrobormide, phosphate, sulfonate, acetate, oxalate, tartrate, citrate, malate, glutamate or aspartate.

2-hydroxy-3-isopropyl-5,6-dimethylpyrazine used in the present invention can be produced by the method disclosed in the above reference, namely, by condensing 2,3-butanedione with valineamide, which is an $\alpha$-amino acid amide, in the presence of a tertiary amine such as triethylamine.

The pharmacological activites and toxicity of 2-hydroxy-3-isopropyl-5,6-dimethylpyrazine hydrochloride of the present invention are illustrated hereinbelow.

EXAMPLE 1

Inhibitory effect on blood platelet aggregation:

(1) Effect in vitro:

A solution of agents to be tested (final concentration 100 $\mu$M) was added to platelet-rich rabbit plasma to which had been added 3.8% sodium citrate (1/10 v/v) and the mixture was incubated at 37° C. for 3 minutes. An aggregating agent, adenosine-5'-diphosphate (final concentration 2.5 $\mu$M), was added thereto and the platelet aggregating potential was measured with an aggregometer.

The results are shown in Table 1. The compound of the present invention shows a distinct inhibitory effect on blood platelet aggregation. However, various control agents, namely tetramethylpyrazine, ticlopidine and acetyl salicylic acid have no inhibitory effect.

TABLE 1

| Compound | Inhibition Ratio on Platelet Aggregation % (Mean ± S.E) |
|---|---|
| Present compound | 69.6 ± 5.4 (5)* |
| Tetramethyl pyrazine | 3.0 ± 1.6 (3)* |
| Ticlopidine | −1.2 ± 1.2 (3)* |
| Acetyl salicylic acid | −0.6 ± 0.6 (3)* |

*( ): numbers of tests (2) Effect in vivo:

Male Wistar rats, five animals in a group, were administered per orally the agents to be tested. After one hour, *E. coli* lipopolysaccharide (5 mg/kg) was injected intraperitoneally and 3 hours thereafter blood samples were collected and measured as to the number of platelets in the circulating blood to determine the ratio of platelets pre- and post-administration of the agents. The tests were repeated twice. The results are shown in Table 2. A marked decrease in the number of platelets is found in the control group. On the contrary, administration of the compound of the present invention, 100 mg/kg per orally, inhibits the decrease of platelet number, which is comparable to an oral dose of 200 mg/kg ticlopidine.

TABLE 2

| Compound | Dose mg/kg p.o. | Number of Platelets (%) | |
|---|---|---|---|
| | | Exp. 1 | Exp. 2 |
| Control | — | 27.5 ± 5.4 | 35.1 ± 12.3 |
| Present compound | 100 | 58.2 ± 7.8 | 55.9 ± 14.0 |
| Ticlopidine | 200 | 57.9 ± 12.0 | 63.4 ± 19.4 |

EXAMPLE 2

Effect on disseminated intravascular coagulation:

Male Wistar rats, seven animals in a group, were administered per orally the agents (100 mg/kg) to be tested. After one hour, *E. coli* lipopolysaccharide (50 mg/kg) was continuously injected intravenously for four hours. A control group was given physiological saline intravenously under the same conditions.

Blood was collected immediately after finishing the injection to measure the number of platelets, the activated partial thromboplastin time, the prothrombin time and the amount of fibrinogen. The results are shown in Table 3. In the control group, in which *E. coli* lipopolysaccharide was injected, a marked decrease in the number of platelets and the amount of fibrinogen and a marked prolongation of the activated partial thromboplastin time and the prothrombin time are observed. In the model of experimental disseminated intravascular coagulation, the compound of the present invention shows a significant effect against all the factors tested.

TABLE 3

| | Platelet Number ($\times 10^3$/ mm$^3$) | Activated Partial Thromboplastin Time (sec.) | Prothrombin Time (sec.) | Fibrinogen (mg/dl) |
|---|---|---|---|---|
| Control (normal) | 640 ± 58 | 25.5 ± 2.2 | 11.6 ± 0.3 | 17.09 ± 14.4 |
| Control (pathomodel) | 93 ± 26 | 78.6 ± 11.2 | 19.8 ± 3.2 | 32.7 ± 11.5 |

TABLE 3-continued

| | Platelet Number ($\times 10^3$/ mm$^3$) | Activated Partial Thromboplastin Time (sec.) | Prothrombin Time (sec.) | Fibrinogen (mg/dl) |
| --- | --- | --- | --- | --- |
| Present compound | 177 ± 51 | 48.5 ± 7.4 | 14.3 ± 1.4 | 77.2 ± 13.1 |

EXAMPLE 3

Vasodilating activity:

(1) Effect upon intra-arterial administration:

Mongrel dogs anesthetized with urethane (450 mg/kg iv) and α-chlora-lose (45 mg/kg iv) after pretreatment with morphine (1.5 mg/kg, sc) were secured in a supine position. Blood from the right femoral artery was introduced into the left femoral artery through a circulation pump and the left hind leg was perfused under constant pressure by connection with a Starling's resistance in an exosomatic circulatory system. The prefusion pressure was set slightly higher than the mean blood pressure of each animal and the change in blood flow upon intra-arterial injection of the test compound was determined.

The results, showing specific activity as compared with a value indicating the degree of increase in the amount of blood flow by papaverine (30 μg, iv) as 100%, are shown in Table 4. The compound of the present invention shows a markedly stronger vasodilating activity than that of the control drug, tetramethylpyrazine.

TABLE 4

| Compound | Dose (μg, i.a.) | Vasodilating Activity % |
| --- | --- | --- |
| Present compound | 100 | 100.7 ± 19.1* |
| Tetramethylpyrazine | 100 | 19.3 ± 0.9* |

*mean ± S.E. for 3 animals (2) Effect upon intravenous administration:

A cuff-type probe for measuring blood flow was applied to the left vertebral artery, the left anterior descending coronary artery, the left renal artery and the right femoral artery of a mongrel dog anesthetized in in the same way as hereinabove and the blood flow was continuously measured. The blood pressure was monitored by a pressure transducer connected to a cannula inserted into the left femoral artery, and the heart rate was monitored through a tachometer by triggering the R-wave of lead II of an electrocardiograph. The agent to be tested was injected into the left venous cephalica. The results are shown in FIG. 1, in which the ordinate indicates the response ratio and the abscissa indicates dosages by intravenous administration, and in which ● : vertebral arterial blood flow;
▲ : coronary arterial blood flow;
■ : femoral arterial blood flow;
□ : renal arterial blood flow;
○ : mean blood pressure; and
△ : heart rate.

The compound of the present invention does not affect the renal arterial blood flow and but rather increases blood flow in the vertebral artery, in the coronary artery and in the femoral artery. Selective effects on the vertebral arterial blood flow and the coronary arterial blood flow are observed, and so the process of the present invention is useful for the treatment of brain and heart haemodynamic disorders.

EXAMPLE 4

Protective effect against anoxia:

Male ddY strain mice, 12 animals in a group, were put into an observation chamber filled with 100% carbon dioxide gas, and the survival time was observed for signs of apnea. The present compound and a control were administered per orally 30 or 60 mins. before the test. The results are shown in Table 5.

Significant prolongation of survival time is observed upon pretreatment with the compound of the present invention.

TABLE 5

| Compound | Dose mg/kg p.o. | Pretreatment Time (min.) | Survival Time (sec.) |
| --- | --- | --- | --- |
| Control | — | 30 | 29.1 ± 0.5* |
| Present compound | 200 | 30 | 42.7 ± 1.6* |
| Control | — | 60 | 31.6 ± 0.6* |
| Present compound | 200 | 60 | 48.1 ± 1.9* |

*mean ± S.E.

EXAMPLE 5

Effect against platelet activated factor (PAF)-induced shock:

Male ddY strain mice, male, 10 animals in a group, were administered per orally the compound of the present invention (100 mg/kg), and after one hour PAF (60 μg/kg) was administered intravenously to determine the ratio of mortality. The results are shown in Table 6, which shows the protective action of the compound of the present invention against PAF-induced shock.

TABLE 6

| | Mortality | |
| --- | --- | --- |
| | Experiment 1 | Experiment 2 |
| Control | 9/10 | 10/10 |
| Present compound | 1/10 | 3/10 |

EXAMPLE 6

Acute toxicity:

Male ddY mice and male Wister rats, were administered intravenously the compound of the present invention to test its acute toxicity. The LD$_{50}$ dose was approximately 200 mg/kg and no death was observed at an intravenous dosage of 100 mg/kg in mice. Rats can be dosed only up to 50 mg/kg due to the solubility of the compound, and no death was observed at a dosage of 50 mg/kg intravenously. The LD$_{50}$ oral dosages were 555 mg/kg for mice and 903 mg/kg for rats.

EXAMPLE 7

Cytotoxicity:

To L5178Y murine lymphoblastoma ($2 \times 10^4$ cells/ml) suspended in a medium (27 ml) comprising Fischer's culture medium including 10% bovine serum, were added test agents in solution (0.3 ml) diluted with a culture medium and the material was incubated at 37° C. for 18 hours. Growth of the cells was determined by color change. Growth inhibition of the cells was not observed at any concentration of 20 μg/ml and 100 μg/ml of the compound of the present invention, and so no cytotoxicity was observed.

EXAMPLE 8

Mutagenicity:

A backward mutation test using microorganism strains TA100, TA1535, WP2 uvr A, TA98, TA1537 and TA1538 was performed by the method according to Iyer et al. [N. Y. Iyer and W. Szybalski, Appl. Microbiol., 6: 37 (1958)]. The test agents were tenfold diluted in six stages of concentration of 0.00333–333 μg/disc. No mutagenesis was found at any concentration of the compound of the present invention. Also no mutagenesis was observed under conditions of metabolic activation using an S-9 mixture.

It is thus demonstrated that 2-hydroxy-3-isopropyl-5,6-dimethylpyrazine or a hydrate or a pharmaceutically acceptable non-toxic salt thereof has an inhibitory effect on blood platelet aggregation, a vasodilating activity, and a protective effect against anoxia, with low toxicity, and so can be used as an agent for the treatment of haemodynamic and metabolic disorders.

The compound of the present invention can be prescribed for human use by its formula per se or in various forms of administration, by various routes, e.g. orally or parenterally such as intramuscular, subcutaneous, intravenous, rectal or cutaneous, preferably orally, with a daily per oral dosage level of 1–600 mg per person, which is to say about 0.02–12 mg/kg of human body weight per day per orally, preferably about 0.5 mg/kg per day per orally, or about 0.5–300 mg/person per day or about 0.01–6 mg/kg per day parenterally. These figures assume a human body weight of 50 kg.

It can be administered in solid form, as tablets, sugar-coated tablets, film tablets, hard or soft capsules, troches, pills, granules or powders; in semi-solid form such as suppositories, cataplasms and ointments; or in liquid form such as injectable solutions or suspensions, syrups, inhalants, emulsions or ingestible suspensions. The compound can be prepared in the above formulations as the compound per se or can be mixed with other components and/or excipients.

EXAMPLE 9

Injectable solution:
2-hydroxy-3-isopropyl-5,6-dimethylpyrazine hydrochloride (10 mg) was dissolved in distilled water for injection (20 ml), adjusted to a concentration of 0.5 mg/ml, sterilized, and filled in a quantity of 1 ml in an ampule as an injectable solution.

EXAMPLE 10

Tablet:
2-hydroxy-3-isopropyl-5,6-dimethylpyrazine hydrochloride: 50 mg
lactose: 80 mg
crystalline cellulose: 40 mg
magnesium stearate: 0.5 mg
talcum: 29.5 mg Tablets (200 mg/tablet) comprising the above composition were prepared by dry tabletting.

EXAMPLE 11

Drip infusion:
An injectable liquid composition was prepared by dissolving 2-hydroxy-3-isopropyl-5,6-dimethylpyrazine hydrochloride (10 mg) in 5% glucose solution (250 ml) to prepare a drip infusion.

What is claimed is:

1. A method of inhibiting blood platelet aggregation in humans, comprising administering to a human in the need of the same an effective amount of 2-hydroxy-3-isopropyl-5,6-dimethylpyrazine or a hydrate or a pharmaceutically acceptable non-toxic salt thereof, said amount being effective to inhibit blood platelet aggregation in a human.

2. A method as claimed in claim 1, in which said administration is effected orally and said amount is about 0.02–12 mg/kg body weight per day.

3. A method as claimed in claim 1, in which said administration is effected parenterally and said amount is about 0.01–6 mg/kg of body weight per day.

4. A method for promoting vasodilation in humans, comprising administering to a human in need of the same an effective amount of 2-hydroxy-3-isopropyl-5,6-dimethylpyrazine or a hydrate or a pharmaceutically acceptable non-toxic salt thereof, said amount being effective to promote vasodilation in a human.

5. A method as claimed in claim 4, in which said administration is effected orally and said amount is about 0.02–12 mg/kg body weight per day.

6. A method as claimed in claim 4, in which said administration is effected parenterally and said amount is about 0.01–6 mg/kg of body weight per day.

* * * * *

UNITED STATES PATENT AND TRADEMARK OFFICE
CERTIFICATE OF CORRECTION

PATENT NO. : 4,721,713

DATED : January 26, 1988

INVENTOR(S) : Eiichi Hayashi et al.

It is certified that error appears in the above-identified patent and that said Letters Patent is hereby corrected as shown below:

On the Title Pate, delete Item [30] Foreign Application Priority Date.

Signed and Sealed this

Twelfth Day of July, 1988

Attest:

DONALD J. QUIGG

Attesting Officer

Commissioner of Patents and Trademarks